United States Patent [19]

Baldwin et al.

[11] Patent Number: 5,308,842
[45] Date of Patent: May 3, 1994

[54] TRICYCLIC DERIVATIVES OF THE THIENODIAZOCINE AND THIENOTHIADIAZOCINE CLASSES OF COMPOUNDS

[75] Inventors: John J. Baldwin, Gwynedd Valley; Gerald S. Ponticello, Lansdale, both of Pa.

[73] Assignee: Merck & Co., Inc., Rahway, N.J.

[21] Appl. No.: 59,793

[22] Filed: May 10, 1993

Related U.S. Application Data

[63] Continuation-in-part of Ser. No. 942,560, Sep. 9, 1992, abandoned.

[51] Int. Cl.⁵ ............... C07D 495/18; C07D 513/18; A61K 31/54; A61K 31/495
[52] U.S. Cl. ............... 514/224.5; 514/220; 514/233.2; 514/250; 540/496; 540/497; 540/556; 544/33; 544/115; 544/346
[58] Field of Search ............ 514/220, 224.5, 233.2, 514/250; 540/496, 497, 556; 544/33, 115, 346

[56] References Cited

U.S. PATENT DOCUMENTS 4,797,413  1/1989  Baldwin et al. .................. 514/432

FOREIGN PATENT DOCUMENTS

91/15486  10/1991  World Int. Prop. O.

*Primary Examiner*—John M. Ford
*Attorney, Agent, or Firm*—Sylvia A. Ayler; Mark R. Daniel; Joseph F. DiPrima

[57] ABSTRACT

Conformationally constrained tricyclic derivatives of the thienodiazocine and thienothiadiazocine classes of compounds and ring homologs thereof are topically effective carbonic anhydrase inhibitors useful in the treatment of ocular hypertension and glaucoma associated therewith. The compounds are of general structure

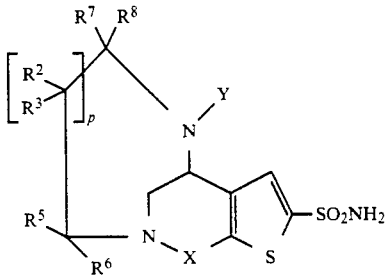

5 Claims, No Drawings 5,308,842

TRICYCLIC DERIVATIVES OF THE THIENODIAZOCINE AND THIENOTHIADIAZOCINE CLASSES OF COMPOUNDS

BACKGROUND OF THE INVENTION

This application is a continuation-in-part of copending application, Ser. No. 07/942,560, filed Sep. 9, 1992 now abandoned.

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many $\beta$-adrenergic blocking agents are effective in reducing intraocular pressure. Many of these agents, however, also have other characteristics, e.g. membrane stabilizing activity, that are not acceptable for chronic ocular use. (S)-1-tert-Butylamino[(4-morpholino-1,2,5-thiadiazol-3-yl)oxy]-2-propanol, a $\beta$-adrenergic blocking agent, was found to reduce intraocular pressure and to be devoid of many unwanted side effects associated with pilocarpine and, in addition, to possess advantages over many other $\beta$-adrenergic blocking agents, e.g. to be devoid of local anesthetic properties, to have a long duration of activity, and to display minimal tolerance.

Although pilocarpine, physostigmine and the $\beta$-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof. Benzothiophene-2-sulfonamides, benzenesulfonylthiophene-2-sulfonamides, and thieno[2,3-b]thiopyran-2-sulfonamides are also reported to be carbonic anhydrase inhibitors topically effective in reducing intraocular pressure in U.S. Pat. Nos. 4,668,697; 4,585,787; and 4,797,413, respectively.

SUMMARY OF THE INVENTION

This invention relates to novel conformationally constrained tricyclic derivatives of the thienodiazocine and thienothiadiazocine classes of compounds and ring homologs thereof of the structural formula

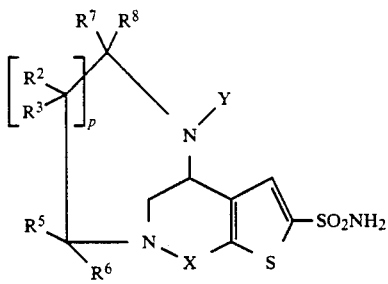

which are topically effective carbonic anhydrase inhibitors useful in the treatment of ocular hypertension and glaucoma.

This invention also relates to ophthalmic formulations comprising at least one of the novel compounds as active ingredient either alone or in combination with other ophthalmic medicaments such as pilocarpine, timolol or enaliprilat.

The invention also relates to a method of treating ocular hypertension and glaucoma associated therewith which comprises the topical ocular administration of a novel compound of this invention to a patient in need of such treatment.

DETAILED DESCRIPTION OF THE INVENTION

The novel compounds of the present invention have the structural formula

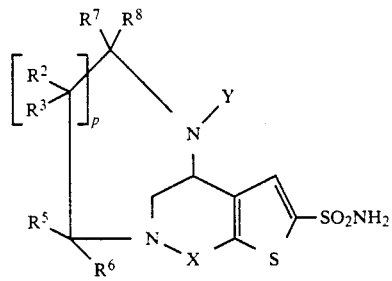

or an ophthalmologically acceptable salt thereof wherein:
Y is —H or

R is hydrogen or $C_{1-3}$alkyl;
$R_1$ is
1) H;
2) $C_{1-6}$alkyl, $C_{1-6}$alkenyl or $C_{1-6}$alkyl substituted with F, OH, $C_{1-5}$alkylS(O)$_m$ or $C_{1-5}$alkyl—O—;
3) phenyl or phenyl-$C_{1-3}$ alkyl wherein the phenyl groups are unsubstituted or substituted by $C_{1-3}$ alkyl, halogen, $CF_3$, OH, or $C_{1-3}$alkoxy;

$R_2$, $R_3$, and $R_5$ are independently H or lower alkyl, preferably $C_{1-4}$alkyl; $R^6$ is H, $C_{1-4}$ alkyl, or $C_{2-4}$ alkenyl or lower alkyl substituted with hydroxy, $C_{1-4}$ alkoxy, hydroxy-$C_{1-4}$ alkoxy, $C_{2-4}$ alkenyloxy, $C_{1-4}$ alkoxy-$C_{1-4}$ alkoxy, hydroxy-$C_{1-4}$ alkoxy-$C_{1-4}$ alkoxy, $C_{1-4}$ alkylamino, di($C_{1-4}$ alkyl)amino, hydroxyalkylamino, $C_{1-3}$ alkoxy $C_{1-4}$ alkylamino, hydroxy-$C_{1-4}$ alkloxy-$C_{1-4}$-alkylamino, $C_{1-4}$-alkyl-$S(O)_m$-, hydroxy-$C_{1-4}$ alkyl-$S(O)m$, $C_{1-4}$ alkoxy-$C_{1-4}$ alkyl-$S(O)_m$-, hydroxy-$C_{1-4}$ alkoxy-$C_{1-4}$alkyl-$S(O)_m$-, $C_{1-4}$ alkyl-$S(O)_m$-$C_{1-4}$ alkoxy, hydroxy $C_{1-4}$ alkyl-$S(O)_m$-$C_{1-4}$ alkoxy, $C_{1-4}$-alkyl-$S(O)_m$-$C_{1-4}$-alkyl-$S(O)_m$ or hydroxy-$C_{1-4}$ alkyl-$S(O)_m$-$C_{1-4}$-alkyl-$S(O)_m$ or morpholino;

$R^7$ and $R^8$ are each H or together represent =O;

X is —SO$_2$— or —C(O)—; and m, is independently 0, 1 or 2 and p is 0 or 1.

One embodiment of the novel compounds is that wherein p is 0 to provide compounds of structure

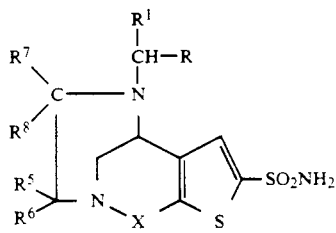

A class of compound within this embodiment is that wherein:

R, $R^1$, and $R^5$ are independently hydrogen or $C_{1-4}$ alkyl; $R^6$ is hydrogen, $C_{1-4}$ alkyl either unsubstituted or substituted with di($C_{1-4}$ alkyl)amino or morpholino; and X is —S(O)$_2$.

The novel process of this invention comprises the steps shown in the following synthetic scheme for p=1.

followed by treatment with an alkylating agent such as ethyl α-bromoacetate. After workup compound 2 is isolated.

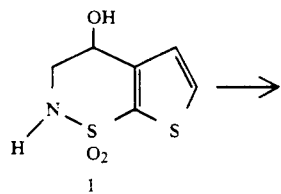

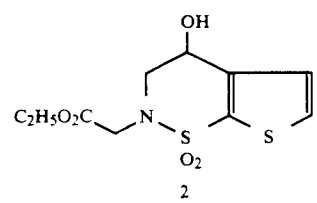

Treatment of 2 with a sulfonyl chloride such as p-toluenesulfonyl chloride in an inert solvent such as CH$_2$Cl$_2$ containing base such as Et$_3$N generates the tosylate in situ which on subsequent reaction with a nucleophile such as ethylamine yields 3.

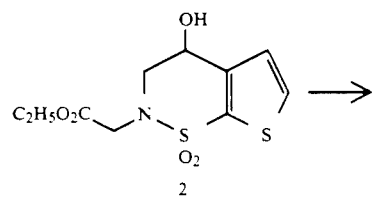

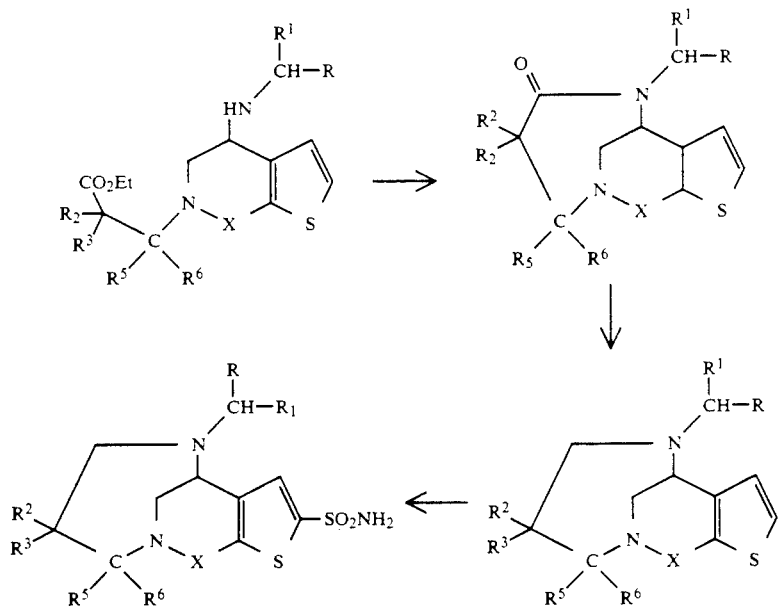

The compounds of the present invention can be prepared by a process typified by the following description which involves as a first step treating 1 with a base, preferably NaH, in a polar solvent such as DMF, for about 5 min. to 1 hour at −30° to 80° C. under N$_2$,

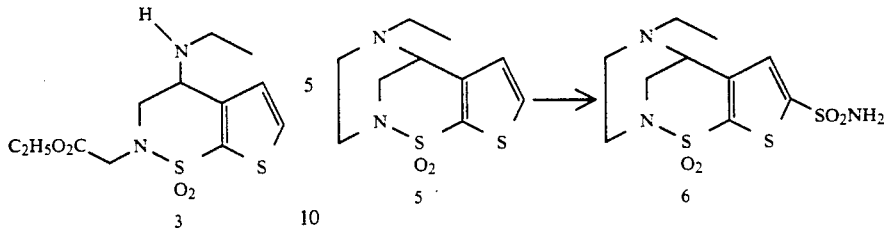

A solution of a trialkylaluminum such as trimethylaluminum in toluene is added to a stirred solution of 3 in an inert solvent such as toluene at about −30° to 25°, preferably, at 0° C. for 2-6 hr, then at room temperature and finally at the reflux temperature for 3-5 hours to yield amide 4.

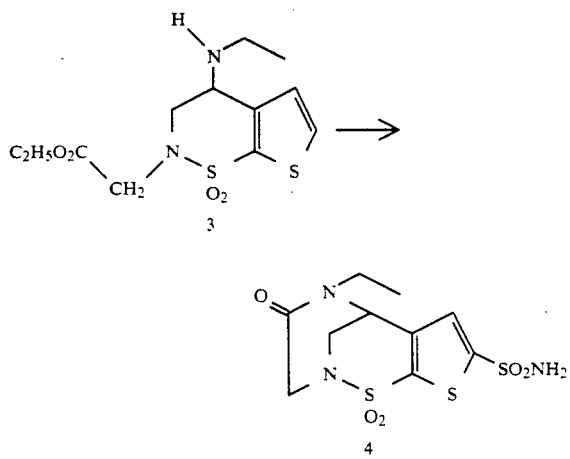

Reduction of 4 using standard reducing agents, such as LAH, BH$_3$•(CH$_3$)$_2$S or NaCNBH$_3$, preferably BH$_3$•(CH$_3$)$_2$S in a polar solvent such as THF at 0° C. to the reflux temperature of the solvent, preferably at reflux under N$_2$ yields the amine 5.

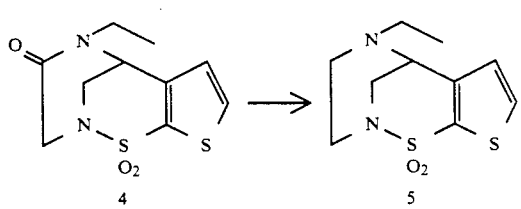

A solution of an alkyl lithium, preferably butyl lithium, in a nonpolar solvent such as, for example, hexane is added to a solution of 5 in a polar solvent such as, for example THF, at lowered temperatures, typically from about −50° C. to about −100° C., preferably at about −78° C. After from about 10 min. to 2 hours at this temperature, SO$_2$ is introduced over the surface of the cold stirred mixture for about 1 min to about 10 min. The solvent is removed and the residue is dissolved in a weakly basic aqueous solution such as an aqueous sodium acetate solution and hydroxylamine-O-sulfonic acid is added and the resulting mixture is stirred for about 3-15 hours at ambient temperature. The mixture is then adjusted to about pH 7.5 by addition of base, preferably NaHCO$_3$, to give the compound 6.

In a modification of the foregoing process the amino function is installed via a Ritter reaction before the alkoxycarbonyl group is substituted on the ring nitrogen as follows:

Compound 1 is treated with sulfuric acid in acetonitrile at 0° C. to ambient temperature over a ½ to 5 hr period followed by pouring into water. After workup compound 7 is isolated.

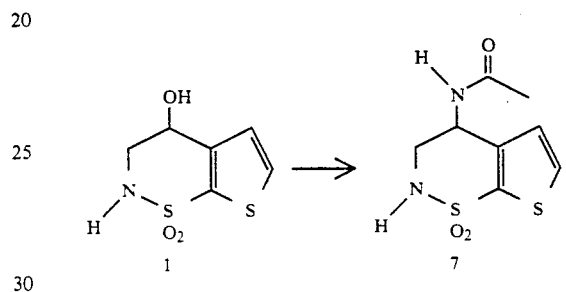

Treatment of 7 with a standard reducing agent, such as LAH, BH$_3$•(CH$_3$)$_2$S or NaCNBH$_3$, preferably BH$_3$•(CH$_3$)$_2$S in a solvent such as THF at 0° C. to the reflux temperature of the solvent, preferably at reflux under N$_2$ yields the amine 8.

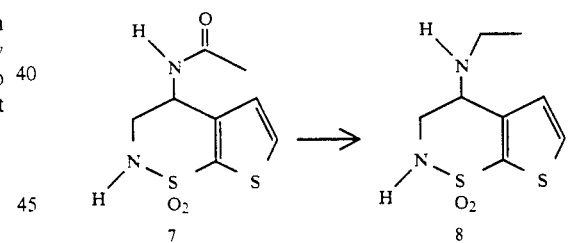

Alkylation of 8 involves reaction with a base, preferably NaH, in a polar solvent such as DMF, for about 5 min. to 1 hour at −30° to 80° C. under N$_2$, followed by treatment with an alkylating agent such as ethyl bromoacetate. Workup gives compound 3.

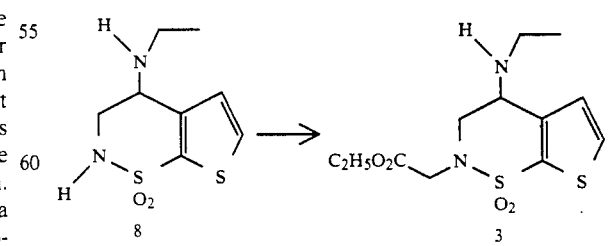

The remainder of the synthesis is as described previously.

Acid hydrolysis of 7 in 12N NCl/methanol at reflux for 1 hour

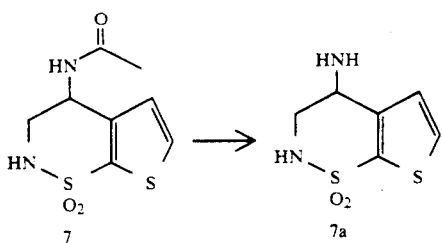

followed by treatment with NaHCO₃ gives compound 7a which can be used in place of compound 8 in the remainder of the synthesis as described.

The novel topical ophthalmic formulation of this invention comprises one of the novel compounds of this invention as active ingredient either alone or in combination with a β-adrenergic blocking agent such as timolol maleate, a parasympathomimetic agent such as pilocarpine or an ophthalmologically active prostaglandin analog. In such combinations the two active agents are present in approximately pharmacologically equal amounts. The active ingredients are present at a concentration of about 0.1% to about 5%, preferably about 0.2 to 1% by weight/volume. The ophthalmic formulation vehicle at about pH 4.5-9 is an aqueous solution, an ointment, a gel or an aqueous solution that gels on contact with the eye.

The novel method of treatment of this invention comprises the treatment of elevated intraocular pressure in a mammalian species by the topical ocular administration of a novel compound of this invention or a pharmaceutical formulation thereof. Of primary concern is the treatment by topical ocular administration of from about 0.1 to about 25 mg and especially from about 0.2 to about 10 mg of such compound per day, either by single dose or on a 2 to 4 dose per day regimen.

The following examples illustrate the present invention without, however, limiting the same thereto.

EXAMPLE 1

5-Ethyl-2H-2,6-methano-3,4,5,6-tetrahydrothieno[3,2-g]-1,2,5-thiadiazocine-8-sulfonamide-1,1-dioxide Step A:

Preparation of ethyl 3,4-Dihydro-2-(carboxy-methyl)-4-hydroxy-2H-thieno[3,2-e]-1,2-thiazine-1,1-dioxide (2)

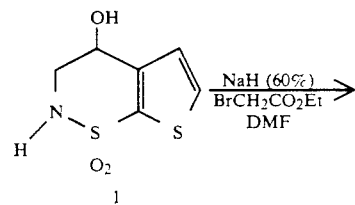

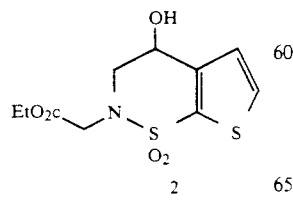

To a solution of 3,4-dihydro-4-hydroxy-2H-thieno[3,2-e]-1,2-thiazine-1,1-dioxide (2.75 g, 1.34 mmol) in aqueous DMF (40 ml) cooled to 0° C. is added NaH (60%) oil dispersion, 1.18 g, 29.5 mmol), followed by ethyl α-bromoacetate (3.36 g, 20.1 mmol). The reaction mixture is stirred at ambient temperature for 4 h, and then poured into ice and extracted with EtOAc (3×). Evaporation of the organic layer followed by chromatography in silica gel yields "title" compound.

Step B:

Preparation of 3,4-dihydro-2-ethoxycarbonylmethyl)-4-ethylamino-2H-thieno[3,2-e]-1,2-thiazine-1,1-dioxide (3)

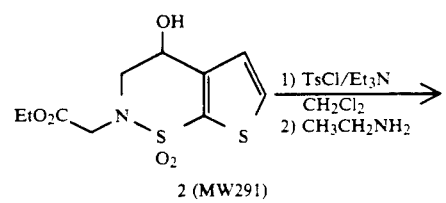

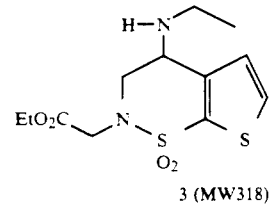

Compound 2 (2.43 g, 9.13 mmol) is dissolved in CH₂Cl₂ (50 ml) containing triethylamine (TEA) (1.86 g, 18.3 mmol). The mixture is cooled to −30° C. and a solution of p-toluenesulfonyl chloride (3.5 g, 18.3 mmol) in CH₂Cl₂ (10 ml) is added dropwise over 5 minutes. The mixture is allowed to warm to 0° C. gradually over 4.5 h, after which time ethylamine (5 ml) is added and the mixture is heated to 50° C. for 4 h and then stirred at ambient temperature overnight. The mixture is poured into water, extracted with EtOAc, dried and concentrated to dryness. The residue is chromatographed on silica gel to yield 3.

Step C:

Preparation of 5-ethyl-2H-2,6-methano-4-oxo-3,4,5,6-tetrahydro-thieno[3,2-g]-1,2,5-thiadiazocine-1,1-dioxide (4)

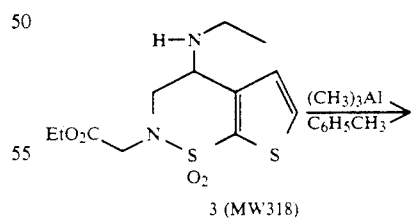

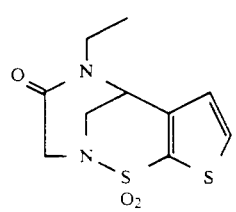

A solution of (CH₃)₃Al in toluene (23 ml, 2M, 46 mmol) is added to a stirred solution of 3 (7.3 g, 23 mmol) in toluene (575 ml) at 0° C. After heating to ambient temperature, the reaction mixture is heated at reflux for 4 h then cooled in an ice batch and treated with 3N HCl (100 ml). The acid layer is diluted with H₂O (50 ml) and extracted with EtOAc (3×). The organic extracts are washed with water, brine, dried, filtered and concentrated to dryness to yield 4.

Step D:

Preparation of
5-ethyl-2H-2,6-methano-3,4,5,6-tetrahydrothieno[3,2-g]-1,2,5-thiadiazocine-1,1-dioxide (5)

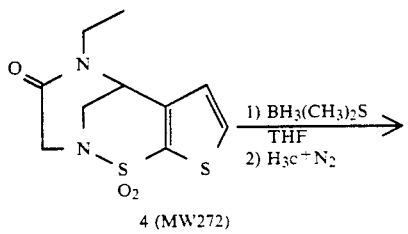

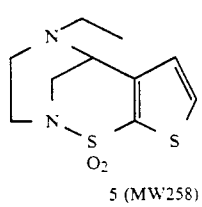

A solution of 4 (0.76 g, 2.8 mmol) and borane-dimethylsulfide (0.84 ml, 10M in THF, 8.4 mmol) in THF (11 ml) is heated under reflux for 2 h under a N₂ atmosphere. The solvent is removed and the residue is heated with 6N HCl (8.5 ml) for 20 minutes to destroy the amine borane complex. The cooled mixture is neutralized with aqueous sodium bicarbonate solution and extracted with ethyl acetate. The organic extract is dried over anhydrous sodium sulfate, filtered and evaporated under reduced pressure to yield crude 5. The residue is chromatographed on silica gel to yield purified 5.

Step E:

Preparation of
5-ethyl-2H-2,6-methano-3,4,5,6-tetrahydrothieno[3,2-g]-1,2,5-thiadiazocine-8-sulfon-amide-1,1-dioxide (6)

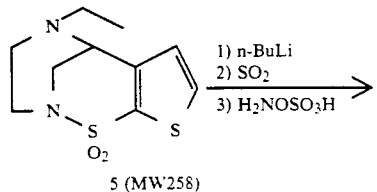

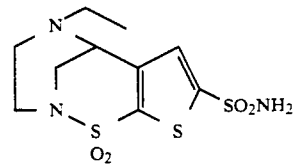

A solution of n-BuLi in hexane (8 ml, 2.5M, 20 mmol) is added to a stirred solution of 5 (4.4 g, 17 mmol) in THF (150 ml) at −78° C. After stirring at this temperature for 2 h, sulfur dioxide is introduced over the surface of the stirred reaction mixture for 20 minutes. The reaction mixture is stirred an additional 0.25 h at this temperature and allowed to warm to ambient temperature. The solvent is removed under reduced pressure and the residue is dissolved in a solution of NaOAc•3H₂O (6.5 g, 48 mmol) in H₂O (60 ml) at 0° C. Hydroxylamine-O-sulfonic acid (4.6 g, 41 mmol) is added and the mixture is stirred overnight at ambient temperature. The mixture is treated with a solution of saturated sodium bicarbonate (50 ml), diluted with water (1500 ml) and extracted with EtOAc (3×). The organic extracts are washed with brine, dried over anhydrous sodium sulfate, filtered and concentrated to dryness. The residue is chromatographed on silica gel to yield 6.

EXAMPLE 2

5-Ethyl-2H-2,6-methano-3,4,5,6-tetrahydrothieno[3,2-g]-1,2,5-thiadiazocine-8-sulfonamide-1,1-dioxide Step A: Preparation of
4-acetamido-3,4-dihydro-2H-thieno[3,2-e]-1,2-thiazine-1,1-dioxide

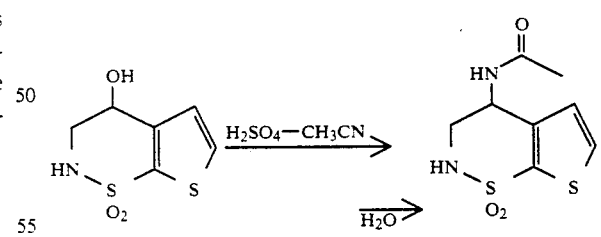

A solution of 3,4-dihydro-4-hydroxy-2H-thieno[3,2-e]-1,2-thiazine-1,1-dioxide (10.26 g, 0.05 mol) in acetonitrile (100 ml) was cooled to 0° C. Then concentrated sulfuric acid (26.6 ml, 0.50 mol) was added dropwise over ½ hr. at 0° to 5° C. The reaction mixture was stirred for ½ hr. at 5° C. and for 4 hrs. at ambient temperature. The resulting solution was poured into ice water (200 ml). A pale beige solid precipitated and was filtered and dried. Wt. was 10.2 g. Yield 83%.

Step B: Preparation of 3,4-dihydro-4-ethylamino-2H-thieno[3,2-e]-1,2-thiazine-1,1-dioxide

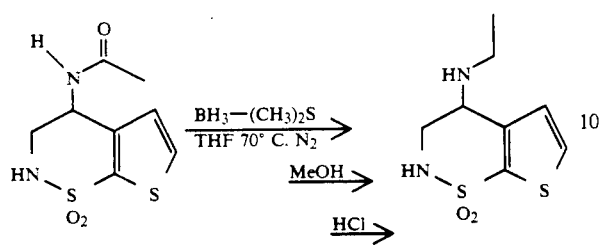

A suspension of 4-acetamido-3,4-dihydro-2H-thieno[3,2-e]-1,2-thiazine-1,1-dioxide (4.93 g, 0.02 mol) in tetrahydrofuran (50 ml) was heated in an oil bath at 70° C. Borane-dimethyl sulfide complex (20.0 ml of 10.0M, 0.20 mol) was added dropwise over ½ hour and the mixture was stirred at 70° C. for 4 hrs. The mixture was cooled in ice and methanol was added (50 ml) dropwise. The volatile solvents were removed in vacuo and the residual oil was heated with 6N hydrochloric acid (50 ml) on the steam bath for ½ hr. Ethyl acetate (200 ml) was added and the mixture was basified with sodium bicarbonate. Methanol (20 ml), was added, the mixture filtered and the aqueous layer was re-extracted with ethyl acetate (100 ml) -methanol (10 ml). The organic solutions were combined, dried and concentrated in vacuo. A colorless viscous oil (4.47 g) was recovered. Yield 96%.

Step C: Preparation of 3,4-dihydro-2-ethoxycarbonylmethyl-4-ethylamino-2H-thieno[3,2-e]-1,2-thiazine-1,1-dioxide

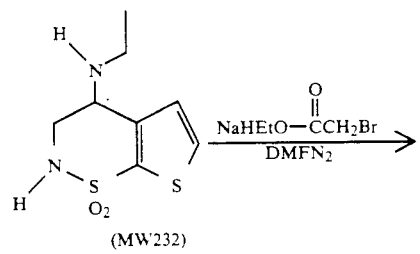

(MW232)

Under a nitrogen atmosphere, sodium hydride (0.44 g of 60% suspension in mineral oil, 0.011 mol) was washed free of mineral oil with petroleum ether. A solution of 3,4-dihydro-4-ethylamino-2H-thieno[3,2-e]-1,2-thiazine-1,1-dioxide (2.32 g, 0.01 mol) in dimethylformamide (10 ml) was added dropwise with stirring over ¼ hr. Stirring was continued for another ½ hr in the cooling bath. Then ethyl bromoacetate (1.25 ml, 0.011 mol) was added and the mixture was stirred for ¼ hr. with cooling and 1 ¾ hrs. at ambient temperature. The volatile components were removed under high vacuum. The oil-solid residue was extracted with ethyl acetate (2×25 ml). The combined extracts were washed with saturated NaCl, dried, filtered and concentrated in vacuo to a viscous yellow oil (2.75 g). Yield was 86%.

Step D: Preparation of 5-ethyl-2H-2,6-methano-4-oxo-3,4,5,6-tetrahydrothieno-[3,2-g]-1,2,5-thiadiazocine-1,1-dioxide

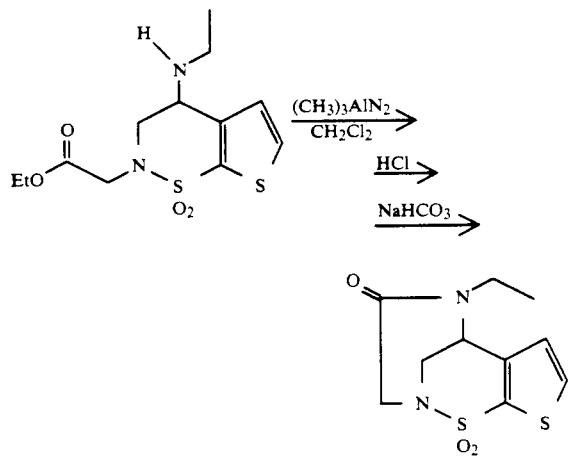

To a stirred solution of 2-ethoxycarbonylmethyl-4-ethylamino-3,4-dihydro-2H-thieno[3,2-e]-1,2-thiazine-1,1-dioxide (8.88 g, 0.0279 mol) in methylene chloride (50 ml) cooled in ice was added trimethylaluminum (21.0 ml of a 2.0M solution in hexane, 0.042 mol) dropwise over several minutes. The resulting solution was stirred to ambient temperature overnight. The solution was cooled and HCl (15 ml of 3N, 0.045 mol) was added dropwise. Ethyl acetate (100 ml) was added followed by NaHCO₃ to basify the mixture. The mixture was filtered. The organic solution was separated, washed with saturated sodium chloride, dried, filtered and concentrated in vacuo to a viscous amber gum. Wt. was 6.8 g. Yield 89%.

Step E: Preparation of 5-ethyl-2H-2,6-methano-3,4,5,6-tetrahydrothieno[3,2-g]-1,2,5-thiadiazocine-1,1-dioxide

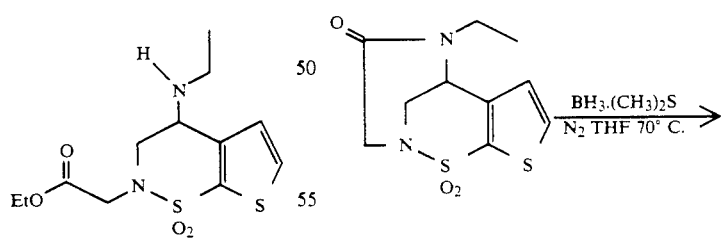

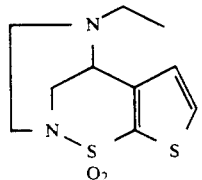

5-Ethyl-2H-2,6-methano-4-oxo-3,4,5,6-tetrahydrothieno[3,2-g]-1,2,5-thiadiazocine-1,1-dioxide (8.7 g, 0.0319 mol) was dissolved in tetrahydrofuran (80 ml) and the solution was heated to 70° C. Borane-dimethyl sulfide (31.9 ml of 10.0 M complex, 0.319 mol) was added dropwise over ¼ hr and the mixture was stirred at 70° C. for 3 ½ hrs. The mixture was distilled to about ½ volume, cooled in ice and decomposed with methanol (80 ml) added dropwise. The volatile components were removed in vacuo and the residual oil was heated on the steam bath with 6N hydrochloric acid (80 ml) for ¾ hr. The cooled mixture was diluted with ethyl acetate (100 ml), basified with NaHCO₃ and filtered. The aqueous layer was re-extracted with ethyl acetate and the ethyl acetate solutions were dried, filtered and concentrated in vacuo to a pale yellow oil (7.0 g). Chromatography on silica gel gave 4.39 g of a white solid, mp 136°-140° C., Yield 54%.

Step F: Preparation of
5-ethyl-2H-2,6-methano-3,4,5,6-tetrahydrothieno[3,2-g]-1,2,5-thiadiazocine-8-sulfonamide-1,1-dioxide

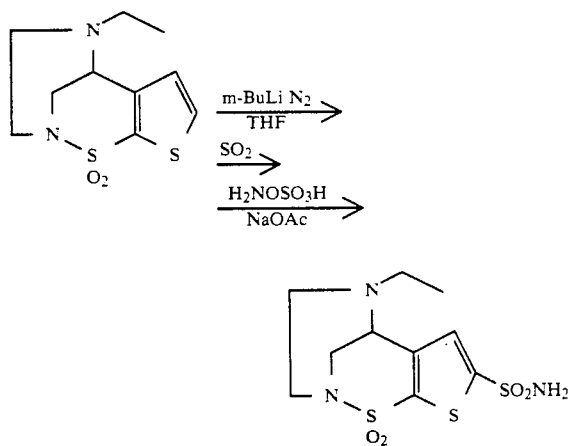

To a stirred solution of 5-ethyl-2H-2,6-methano-3,4,5,6-tetrahydrothieno[3,2-g]-1,2,5-thiadiazocine-1,1-dioxide (3.23 g, 0.0125 mol) in tetrahydrofuran (30 ml) under a nitrogen atmosphere was added n-butyl lithium (5.5 ml, 0.0137 mol of a 2.5M solution in hexane) dropwise over ¼ hr at −78° C. The solution was stirred for 1 hr at −78° C. and then anhydrous sulfur dioxide was blown over the surface of the solution until the mixture became acidic (temperature rose to −40° C. over the ¼ hr. addition). The reaction was stirred for 1 hr. at 40° C. and then the temperature was allowed to rise to 0° C. over ½ hr. The resulting yellow suspension was concentrated to dryness in vacuo. The residual lithio sulfinic acid was taken up in water (30 ml) and tetrahydrofuran (10 ml) containing sodium acetate (2.1 g, 0.025 mol) and hydroxylamine-O-sulfonic acid (2.12 g, 0.0187 mol) was added. The reaction was stirred at ambient temperature overnight. The tetrahydrofuran was removed in vacuo and the oil-water residue was extracted with ethyl acetate (2×75 ml). The combined extracts were dried, filtered and concentrated to a foam (2.5 g). Silica gel chromatography gave a white solid (1.2 g). The hydrochloride salt was prepared in chloroform-methanol to yield 1.18 g, melting slowly >193° C. The compound analyzed for C₁₀H₁₅N₃O₄S₃•HCl.

EXAMPLE 3

5-Ethyl-3-dimethylaminomethyl-2H-2,6-methano-3,4,5,6-tetrahydrothieno[3,2-g]-1,2,5-thiadiazocine-8-sulfonamide-1,1-dioxide (13)

Step A: Preparation of
2-[di(ethoxycarbonyl)methyl]-3,4-dihydro-4-ethylamino-2H-thieno[3,2-e]-1,2-thiazine-1,1-dioxide (8)

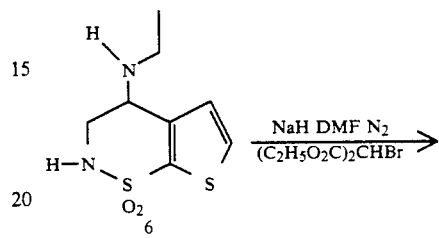

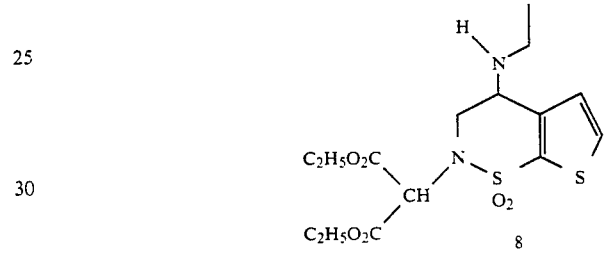

Under a nitrogen atmosphere, sodium hydride (1.6 g of a 60% suspension in mineral oil, 0.04 mol) was washed free of mineral oil with dry petroleum ether and was stirred in dimethylformamide (10 ml). A solution of compound 6 (8.43 g, 0.036 mol) in dimethylformamide (30 ml) was added over several minutes at ice bath temperature and stirring was continued for 1 hr. Then ethyl bromomalonate (9.56 g, 0.04 mol) was added and the mixture was stirred at ambient temperature for 3 hrs and was heated on the steam bath for 1 hr. The solvent was removed in vacuo. Water (50 ml) was added and the mixture was extracted with ethyl acetate (3×50 ml) from which a viscous red oil was recovered. Chromatography on silica gel gave compound 8 as an oil. Wt. is 2.2 g.

Step B: Preparation of
3-ethoxycarbonyl-5-ethyl-2H-2,6-methano-4-oxo-3,4,5,6-tetrahydrothieno[3,2-g]-1,2,5-thiodiazocine-1,1-dioxide (9)

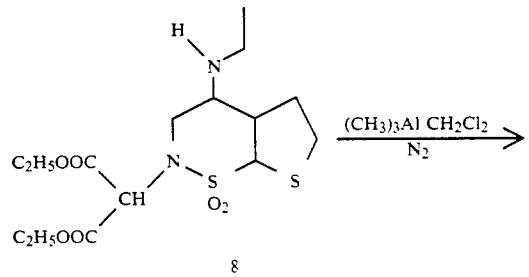

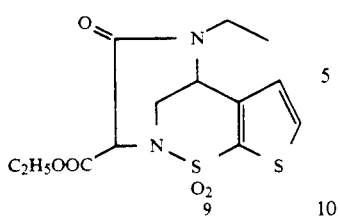

Compound 9 is prepared as described in Example 1, Step C except that compound 8 (2.2 g, 0.0057 mol) is used in place of compound 3. Isolation of product 9 requires two silica gel chromatography separations.

Step C:

Preparation of
3-carboxy-5-ethyl-2H-2,6-methano-4-oxo-3,4,5,6-tetrahydrothieno[3,2-g]-1,2,5-thiadiazocine-1,1-dioxide (10)

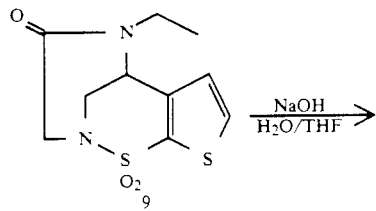

A solution of 9 (1.8 g, 0.0052 mol) in THF (50 ml) is treated with 2N NaOH (50 ml) and is stirred at room temperature. After 3 hrs., the solution is acidified with 3 NHCl (50 ml) and is extracted with ethyl acetate (3×). The combined organic layers are dried, filtered and concentrated to dryness to yield acid 10.

Step D:

Preparation of
3-(N,N-dimethylcarbamoyl)-5-ethyl-2H-2,6-methano-4-oxo-3,4,5,6-tetrahydrothieno[3,2-g]-1,2,5-thiadiazocine-1,1-dioxide (11)

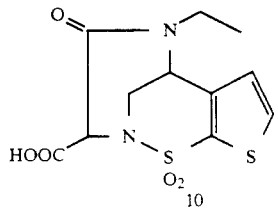

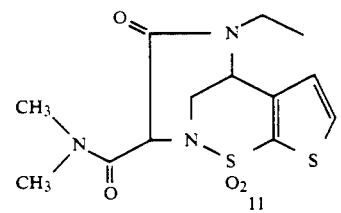

Under a $N_2$ atmosphere, carbonyldiimidazole (8.9 g, 0.055 mol) is added to a solution of 10 (15.8 g, 0.05 mol) in THF (50 ml). After stirring at room temperature for ¾ hr., anhydrous dimethylamine is bubbled into the mixture which is cooled to 0° C. After ¾ hr., the solvent is removed in vacuo and the residue is partitioned between $H_2O$ and EtOAc (3×). The organic extracts are dried, filtered and concentrated to dryness to yield amide 11.

Step E:

Preparation of
3-(N,N-dimethylaminomethyl)-5-ethyl-2H-2,6-methano-3,4,5,6-tetrahydrothieno[3,2-g]-1,2,5-thiodiazocine-1,1-dioxide (12)

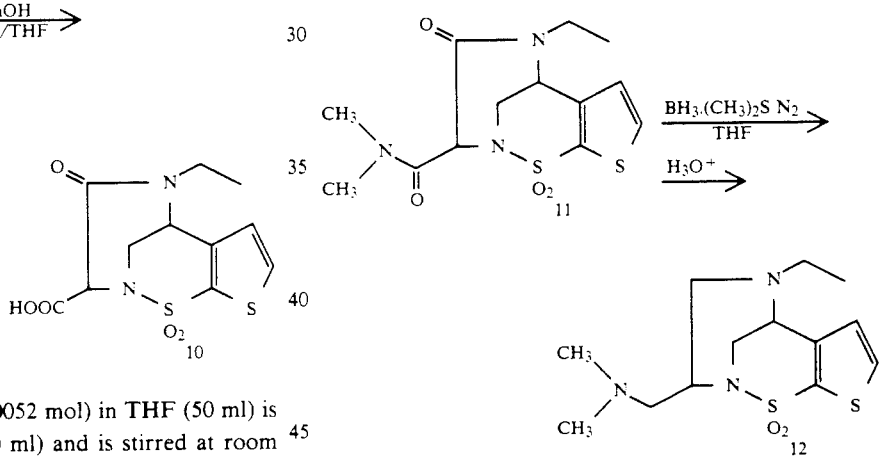

Compound 12 is prepared as described in Example 1, Step D except that Compound 11 is used in place of Compound 4 and the quantity of borane-methyl sulfide complex is doubled.

Step F:

Preparation of
3-(N,N-dimethylaminomethyl)-5-ethyl-2H-2,6-methano-3,4,5,6-tetrahydrothieno[3,2-g]-1,2,5-thiadiazocine-8-sulfonamide-1,1-dioxide (13)

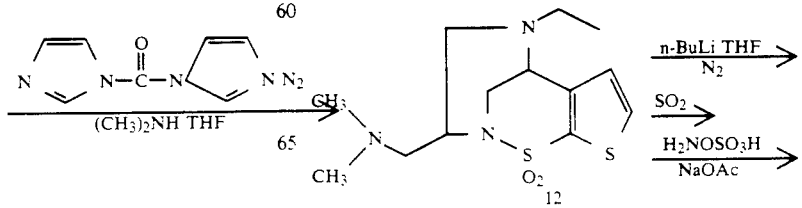

-continued

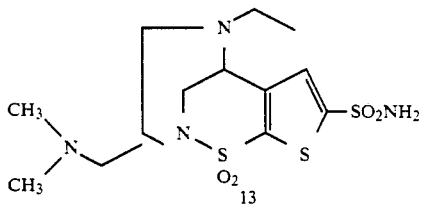

Compound 13 is prepared as described in Example 1, Step E, except that compound 12 is used in place of compound 5.

EXAMPLE 4

5-ethyl-2H-2,6-methano-3-(morpholinomethyl)-3,4,5,6-tetrahydrothieno[3,2-g]-1,2,5-thiadiazocine-8-sulfonamide-1,1-dioxide (16)

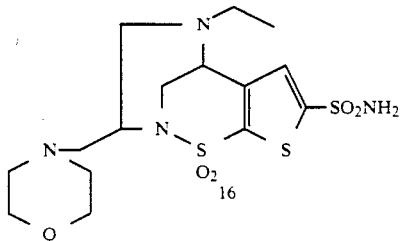

Compound 16 is prepared as described in Example 3, Step D–F using morpholine in place of dimethylamine.

EXAMPLE 5

| Pharmaceutical Formulations | | |
|---|---|---|
| | Aqueous Solution | |
| Active compound | 1 mg | 15 mg |
| Monobasic sodium phosphate 2H$_2$O | 9.38 mg | 6.10 mg |
| Dibasic sodium phosphate .12H$_2$O | 28.48 mg | 16.80 mg |
| Benzalkonium chloride | 0.10 mg | 0.10 mg |
| Water for injection q.s. and. | 1.0 mg | 1.0 mg |

The active compound, phosphate buffer salts, and benzalkonium chloride are added to and dissolved in water. The pH of the composition is adjusted to 6.8–9 and diluted to volume. The composition is rendered sterile by ionizing radiation.

| | Ointment |
|---|---|
| Active compound | 5 mg |
| petrolatium q.s. and | 1 gram |

The compound and the petrolatum are aseptically combined.

What is claimed is:

1. A compound of structural formula:

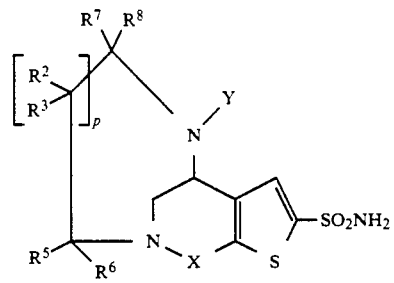

or an ophthalmologically acceptable salt thereof, wherein:
Y is —H or

R is hydrogen or C$_{1-3}$ alkyl;
R$^1$ is
  1) hydrogen,
  2) C$_{1-6}$ alkyl either unsubstituted or substituted with F, OH, C$_{1-5}$ alkyl-S(O)$_m$, or C$_{1-5}$ alkoxy;
  3) C$_{2-5}$ alkenyl;
  4) phenyl or phenyl-C$_{1-3}$ alkyl, where the phenyls are unsubstituted or substituted with C$_{1-3}$ alkyl, C$_l$, Br, F, CF$_3$, OH or C$_{1-3}$ alkoxy;
R$^2$, R$^3$ and R$^5$ are independently hydrogen or C$_{1-4}$ alkyl;
R$^6$ is
  (a) H,
  (b) C$_{1-4}$ alkyl,
  (c) C$_{2-4}$ alkenyl
  (d) C$_{1-4}$ alkyl substituted with
    (1) hydroxy,
    (2) C$_{1-4}$ alkoxy,
    (3) hydroxy-C$_{1-4}$ alkoxy,
    (4) C$_{2-4}$ alkenyloxy,
    (5) C$_{1-4}$-alkoxy-C$_{1-4}$ alkoxy,
    (6) hydroxy-C$_{1-4}$ alkoxy-C$_{1-4}$-alkoxy,
    (7) C$_{1-4}$ alkylamino,
    (8) di(C$_{1-4}$ alkyl)amino,
    (9) hydroxy-C$_{1-4}$ alkylamino,
    (10) C$_{1-3}$ alkoxy-C$_{1-4}$ alkylamino,
    (11) hydroxy-C$_{1-4}$ alkoxy-C$_{1-4}$ alkylamino,
    (12) C$_{1-4}$ alkyl-S(O)$_m$-,
    (13) hydroxy-C$_{1-4}$ alkyl-S(O)$_m$,
    (14) C$_{1-4}$ alkoxy-C$_{1-4}$ alkyl-S(O)m-,
    (15) hydroxy-C$_{1-4}$ alkoxy-C$_{1-4}$ alkyl-S(O)$_m$-,
    (16) C$_{1-4}$-alkyl-S(O)$_m$-C$_{1-4}$ alkoxy,
    (17) hydroxy-C$_{1-4}$-alkyl-S(O)$_m$-C$_{1-4}$ alkoxy,
    (18) C$_{1-4}$ alkyl-S(O)m-C$_{1-4}$ alkyl-S(O)$_m$,
    (19) hydroxy-C$_{1-4}$ alkyl-S(O)m-C$_{1-4}$ alkyl-S(O)m
    or
    (20) morpholino;
R$^7$ and R$^8$ are each hydrogen or together represent=O;
X is —S(O)$_2$— or —C(O)—;
m, is independently 0, 1 or 2; and p is 0 or 1.

2. The compound of claim 1, wherein p is 0.
3. The compound of claim 2 wherein Y is —CHRR$^1$; R, R$^1$, and R$^5$ are independently hydrogen or C$_{1-4}$ alkyl; and R$^6$ is hydrogen, C$_{1-4}$ alkyl either unsubstituted or substituted with di(C$_{1-4}$alkyl) amino or 1-morpholinyl; and X is —S(O)$_2$—.
4. An ophthalmic formulation consisting essentially of an ophthalmologically acceptable carrier and an effective amount of a compound of claim 1.
5. A method of treating ocular hypertension and glaucoma associated therewith which comprises the topical ocular administration, to a member of a mammalian species in need of such treatment, of an effective amount of a compound of claim 1.

* * * * *